United States Patent [19]

Diaz

[11] Patent Number: 4,547,619
[45] Date of Patent: Oct. 15, 1985

[54] PROCESS FOR REMOVAL OF PHENOLIC INHIBITORS FROM POLYMERIZABLE CONJUGATED OLEFIN

[75] Inventor: Zaida Diaz, Houston, Tex.

[73] Assignee: Shell Oil Company, Houston, Tex.

[21] Appl. No.: 685,665

[22] Filed: Dec. 24, 1984

[51] Int. Cl.$^4$ .............................................. C07C 7/12
[52] U.S. Cl. .................... 585/824; 585/826; 208/91
[58] Field of Search .................. 585/824, 826; 208/91

[56] References Cited

U.S. PATENT DOCUMENTS 2,412,504  12/1946  Goldfinger .......................... 585/824
3,240,830  3/1966   Dye ..................................... 585/824

Primary Examiner—D. E. Gantz
Assistant Examiner—Chung K. Pak
Attorney, Agent, or Firm—Ronald R. Reper

[57] ABSTRACT

Method for removal of phenolic polymerization inhibitors from liquid conjugated olefin hydrocarbon by contacting said liquid hydrocarbon with a sorbent material comprising particulate acidified active carbon which sorbent has previously been oxidized by contact with a highly acidic oxidizing fluid. Optionally, after contact with the highly acidic oxidizing fluid the sorbent may be further treated in an alkaline environment with compounds of at least one of alkali metals, alkaline earth metals and ammonia. The sorbent material may be regenerated by heating, or by passing a heated non-oxidizing gas e.g., superheated stream there through.

12 Claims, No Drawings

PROCESS FOR REMOVAL OF PHENOLIC INHIBITORS FROM POLYMERIZABLE CONJUGATED OLEFIN

FIELD OF INVENTION

This invention relates to a process for removing materials which inhibit polymerization from polymerizable conjugated olefin hydrocarbons. The process is particularly useful for removing tertbutyl catechol from butadiene, isoprene and styrene.

BACKGROUND OF THE INVENTION

Conventionally, after their manufacture, conjugated olefins such as aliphatic diolefins and vinyl aromatics often are inhibited with one or more materials to inhibit oxidation and to prevent spontaneous polymerization before it is desired e.g., during transport and storage. Most commonly tert-butyl catechol and hydroquinone are employed in amounts from about 10 to about 200 parts per million (ppm). Although these phenolic inhibitors are innocuous for many downstream process, their presence can complicate the production of high molecular weight materials such as plastics, elastomers, thermoplastic elastomers and the like. The inhibitors can cause excessive consumption of polymerization initiators and result in production of polymeric materials of too high or too low molecular weight, too wide or too narrow molecular weight distribution, unwanted gels and the like.

It has long been industrial practice to remove the phenolic inhibitors such as tert-butyl catechol by washing with caustic solutions, however, that can add unwanted moisture. Another technique is sorbing onto granular alumina, however, the capacity of the alumina is rather low and its sorbency for tert-butyl catechol is poorly regenerable. Accordingly, a simple efficient process to remove the phenolic inhibitor compounds, when their presence is no longer desired, is of great interest.

A sorbent material found to have unique properties is acidified active carbon prepared by contacting particulate active carbon with a highly acidic oxidizing medium. As described in Blytas U.S. Pat. Nos. 4,048,061 and Blytas 4,116,820 (both incorporated herein by reference) acidified active carbon has good utility in sorbing certain metal compounds from hydrocarbon liquids. Further, such acidified active carbons, after having their surface hydrogen ions exchanged by metal cations such as lithium, sodium, potassium and calcium, have been found efficient to remove water from gas streams as described by Mahajan et al, Separation Science and Technology, 17(8), pp 1019-1025 (1982).

SUMMARY OF THE INVENTION

The invention provides a process for reducing the level of phenolic inhibitors in liquid conjugated olefin hydrocarbons which comprises contacting said liquid hydrocarbon with a sorbent material comprising particulate acidified active carbon which sorbent has previously been oxidized by contact with a highly acidic oxidizing fluid and substantially separated from said oxidizing fluid.

The invention further provides a process for reducing the level of phenolic compounds as above wherein the sorbent has been pretreated as described above and said sorbent is then further pretreated in an alkaline environment with a compound of a material selected from alkali metals, alkaline earth metals and ammonia. The invention still further provides a method for regenerating the phenolic compound-containing sorbent which comprises heating the sorbent to an elevated temperature for a time sufficient to strip off the phenolic compounds, optionally in presence of flow of a non-oxidizing gas.

DESCRIPTION OF PREFERRED EMBODIMENTS

The sorbent according to the invention is a porous active carbon which has been pretreated with a strongly acidic oxidizing medium. Although any active carbon can be used, preferably, the activated carbon starting materials are particulate, porous, amorphous solids having a majority (40–100%) of its pores with wide diameter, i.e., greater than about 0.9 nanometers (nm) and preferably in the range from about 1.0 to about 15.0 nm, and most preferably from 1.5 to 10 nm as may be determined by isothermal nitrogen desorption measurement at 195° C. Generally, the pores of the active carbon will be increased in size after treatment with strongly acidic oxidizing medium, particularly in the range from about 1.0–2.5 nm.

The contacting of the above active carbons with an oxidizing agent must be carried out in a strongly acidic medium. In some cases the acid itself may be oxidizing e.g., concentrated nitric acid, oleum and to a lesser extent concentrated sulfuric acid, and mixtures of these. It has been found that the use of strong acids such as concentrated hydrochloric acid upon contacting the activated carbon in the absence of an oxidizing agent, is ineffective to produce sorbents having the high activity and capacity of the sorbents produced according to the invention. It is critical to the sorbent of the invention to have an oxygenated surface formed in the presence of a strong acid medium. A wide variety of known oxidizing agents stable in strongly acidic media are known and include e.g., nitrates such as potassium nitrate, chromates, e.g., chromium oxides, and sodium chromate; dichromates such as potassium dichromate; permanganates such as potassium permanganate and the like. The amount of reactant will vary depending upon the particular active carbon as well as the oxidizing/acidic fluid employed. The reaction fluid may be gaseous e.g., a mixture of oxygen and sulfur trioxide gases, or liquids. Excellent results have been obtained with aqueous acids, e.g., at temperatures from about 50° to about 200° C., and preferably from 80°–160° C. Reaction time to oxidize the surface of the carbon with the acidic media may be from 1–2 minutes to 24 hours or more, preferred times are from about 10 to 60 minutes at temperatures of about 50° to about 200° C. Subatmospheric, atmospheric or superatmospheric pressures may be employed. After the reaction is essentially complete, it is highly desirable to substantially separate the acid from the carbon. Any known technique may be used. Simple water washing until the pH of the wash water is on the order of 2 to 3 or more has proven effective. The washed carbon is then substantially dried preferably at elevated temperature. Temperatures in the range from about 100°–200° C. are suitable. Vacuum may be employed, if desired. Generally speaking, shorter times are employed at the higher temperatures. However, for some applications such as where the hydrocarbon liquids after removal of the tert-butyl catechol may be polymerized in the presence of appreciable undissolved water, e.g., emulsion polymerization, the carbon need not be completely dried but may contain a few percent more of water. After the contacting of the active carbon with the strongly acid oxidizing medium the carbon will ordinarily have an increased oxygen content of from at least about 1% w (on carbon) of oxygen and preferably at least about 3% w.

In a preferred embodiment it has been found that the effectiveness of the acidified active carbon as sorbent for the phenolic inhibitor compounds can be increased if the surface hydrogen ions of the acidic oxygen groups present on the oxidized carbon surfaces are treated in an alkaline environment with a compound of an alkali and/or an alkaline earth metal, or ammonia, and the treated carbon then substantially separated from the alkaline material. Suitable ammonium compounds include the hydroxide, carbonate, bicarbonate, acetate, and like compounds of sodium, potassium, lithium, rubidium, calcium, barium and strontium. Because of availability and generally lower cost, preference is given to sodium, calcium and ammonium compounds.

The conjugated olefins to be treated according to the inhibitor removal process of the invention will generally have atmospheric boiling points in the ranges from about $-5°$ C. to about $+195°$ C. and will include aliphatic diolefins such as butadiene; isoprene, cis-piperylene; trans-piperylene; 2,3 dimethyl-1,3-butadiene; 2-methyl-1,3-pentadiene; 4-methyl-1,3-pentadiene; myrcene; and vinyl aromatic hydrocarbons such as styrene; α-methyl styrene; vinyl toluene; m- and p- divinylbenzene; and mixtures of the foregoing.

The removal process is very suitable for the commercially available aliphatic diolefins butadiene, isoprene and the piperylenes. It is further suitable for commercially available vinyl aromatics such as styrene, α-methyl styrene and divinyl benzene. Of these conjugated olefins, the most significant commercially are butadiene, isoprene and styrene.

Phenolic inhibitors commonly used in conjugated olefin hydrocarbons include the tert-butyl catechol and hydroquinone. Tert-butyl catechol is most widely used. Further, phenolic inhibitors include 2,6-di-tert-butyl p-cresol, 6-tert-butyl m-cresol and pyrogallol.

The contacting of the conjugated olefin with the sorbent according to the invention may take place in any known solids-liquid contacting process e.g., by slurrying with subsequent filtration to separate the solid sorbent, however, preferably, and most conveniently, the inhibitors are removed by passing the conjugated olefin liquid through a bed of the granular sorbent at weight hourly space velocities of 0.1 to about 100 and preferably from about 10 to 75. The contact bed may be in any configuration adapted from the desired flow rate and inhibitor content of the conjugated olefin.

The sorbent is effective at temperatures up to the boiling point of the liquid conjugated olefin. There is no particular lower limit on the temperature. The lower limit is determined by the particular hydrocarbon stream being processed and the temperature at which it solidifies or becomes too viscous to process.

The sorbent is used in typical fashion. It is preferably used in a packed bed or column. The use of dual columns allow one to be regenerated for sorbing additional tert-butyl catechol while the other is sorbing.

The process of this invention is illustrated by the following examples which are provided for illustration and comparative purposes and are not to be construed as limiting the invention.

EXAMPLE I

This example illustrates preparation of the acidified active carbon. A commercially available active carbon available from Calgon Division of Merck chemical having a particle size of 12×40 mesh (US) was contacted with a solution of 430 ml of concentrated (96% w) sulfuric acid and 230 ml of concentrated (70% w) nitric acid in a ratio of 4 ml of solution per gram of carbon at a temperature of about 20°–25° C. which exothermed up to a temperature of about 130° C. After about 20–25 minutes the carbon slurry in acid solution was quenched by pouring said slurry into 3 liters. of deionized water, and the carbon separated fromt the diluted solution. The separated carbon was then washed four times with 3 liters of deionized water until the pH of the final rinse water was 2 or higher, and dried for two to two and one-half hours at 150°–160° C. under a vacuum of about 260 mm absolute. The resulting acidified active carbon (AAC) was then used in the following examples, except as noted.

EXAMPLE II

This example illustrates preparation of a sodium exhanged active carbon. 310 Grams of acidified active carbon prepared according to the procedure of Example I is stirred into 3 l of 1N NaOH and remained in contact, without further stirring for about 22 hours. The sodium exchanged AAC is then rinsed five times each with 3 l of deionized water followed by a single rinse of 3 l of a solution of 60% volume methanol in water, and is dried at a temperature of 130° C. in a vacuum oven (pressure 260 mm absolute) over a weekend (65 hours). The resulting sodium exchanged AAC was then tested for sorbency of tert-butyl catechol as described in the following Example.

EXAMPLE III

In order to compare the sorbency of the AAC, and the sodium exchanged AAC with an alumina sold commercially for tert-buty catechol removal, 1 gram of each sorbent was contacted with 100 g of a solution of 200 parts per million (ppm) tert-butyl catechol in isoprene at 2° C. for a period of 16 hours. After said period of contacting a sample of the isoprene is withdrawn and analyzed for tert-butyl catechol content. From the reduction in tert-butyl catechol the amount of tert-butyl catechol loading on the sorbent is determined. This procedure was repeated to develop several equilibrium sorbent loadings of tert-butyl catechol on the sorbent from which sorption isotherms are developed. Results are shown in Table I along with a single result for active carbon (AC) without the acid treatment.

TABLE I

Removal of tert-butyl catechol (TBC) from isoprene at 2° C.
TBC Loading on Sorbent (g/100 g)

| Equilibrium TBC in isoprene (PPMW) | AC | AAC | Sodium Exchanged AAC | Alcoa Fl Alumina |
|---|---|---|---|---|
| 5 | | 1.9 | 4.4 | 1.3 |
| 10 | | 3.0 | 6.3 | 2.3 |
| 20 | 1.3 | 4.6 | 7.6 | 3.0 |
| 30 | | 5.9 | 8.2 | 3.4 |
| 40 | | — | 8.7 | 3.7 |
| 100 | | — | — | 4.7 |

These data show that the acidified active carbon has a much higher capacity for removing tert-butyl catechol than does the commercially used alumina, which capacity is even further enhanced for the sodium exchanged AAC.

EXAMPLE IV

The procedure of Example II is repeated except that 10 grams of a different batch of AAC is added to 500 ml of 0.2N calcium hydroxide and stirred for 30 hours at room temperature (25° C.). The calcium exchanged AAC is separated by filtration, rinsed with 1 L. of deionized water, then with 600 ml of methanol and dried in a vacuum oven at 100° C. for 16 hours at a pressure of 260 mm absolute. This calcium exchanged carbon too is found to have higher sorption capacity for tert-butyl catechol than the alumina. Following the procedure of Example III, the TBC loading at 5 ppmw equilibrium TBC is isoprene was 2.3 g/100 g; at 10 ppmw the loading was 2.7 g/100 g.

EXAMPLE V

To demonstrate the capacity and regenerability of sorbents according to the invention, isoprene-containing 218 ppm of tert-butyl catechol was flowed through a bed of 51.4 grams of sodium exchanged AAC prepared according to the general procedure of Example II. Samples of the effluent isoprene were analyzed to determine "break through" i.e., the bed weights of conjugated olefin passing through the bed of sodium exchanged AAC before the tert-butyl catechol concentration in the effluent increased to 10 ppm. The "break through" capacity was found to be 160 bed weights. The tert-butyl catechol-containing isoprene continued to flow through the sodium exchanged AAC bed to a total volume of 504 bed weights after which the sodium exchanged AAC was regenerated by heating to a temperature of 300° C. for 16 hours. After this, the bed was cooled and the same fresh isoprene flowed through the bed again. Breakthrough from this regenerated sodium exchanged AAC was about 75 bed weights. This may be compared to a break through of 40 bed weights for alumina regenerated according to the same procedure.

What is claimed is:

1. A process for the removal of phenolic polymerization inhibitors from an inhibitor-containing liquid conjugated olefin hydrocarbon which comprises contacting said liquid hydrocarbon with sorbent material comprising particulate acidified active carbon which sorbent has previously been oxidized by contact with a highly acidic oxidizing fluid and substantially separated from said oxidizing liquid.

2. The process of claim 1, where the sorbent after separation from the highly oxidizing fluid is further treated in an alkaline environment with a compound of a material selected from alkali metals, alkaline earth metals and ammonia.

3. The process of claim 1, wherein the liquid conjugated olefin is a hydrocarbon having an atmospheric boiling point in the range from about −5° to about 195° C.

4. The process of claim 1, wherein the liquid conjugated olefin is an aliphatic diolefin.

5. The process of claim 4, wherein said aliphatic olefin is selected from butadiene, isoprene and the piperylenes.

6. The process of claim 1, wherein the liquid conjugated olefin is a vinyl aromatic hydrocarbon selected from styrene, α-methyl styrene and divinyl benzene.

7. The process of claim 1, wherein the liquid conjugated olefin is selected from butadiene, isoprene and styrene.

8. The process of claim 2, wherein the oxidized sorbent is treated in an alkaline environment with a compound of a material selected from the group consisting of sodium, calcium and ammonia.

9. The process of claim 1, wherein said polymerization inhibitor is selected from the group consisting of tert-butyl catechol and hydroquinone.

10. The process of claim 9, wherein said polymerization inhibitor is tert-butyl catechol.

11. The process of claim 1, wherein after contacting said liquid conjugated olefin with said sorbent for a substantial period of time, the contacting is stopped, the sorbent is heated to a temperature in the range above about 275° C. until substantially all of the phenolic inhibitor is stripped off, the sorbent is cooled to a temperature below about the boiling point of said liquid conjugated olefin, and contacting of said sorbent with said liquid conjugated olefin is resumed.

12. The process of claim 1, wherein after contacting said liquid conjugated olefin with said sorbent for a substantial period of time, the contacting is stopped, a stream of a non-oxidizing gas is passed over the sorbent at a temperature of at least about 200° C. until substantially all of the phenolic inhibitor is stripped off, the flow of the non-oxidizing gas is stopped, and contacting of said sorbent with said liquid is resumed.

* * * * *